United States Patent [19]

Mehta et al.

[11] Patent Number: 5,290,794

[45] Date of Patent: Mar. 1, 1994

[54] SOLUBLE CALCIUM LACTATE ANTIBACTERIAL COMPLEXES AS NON-IRRITATING PARENTERAL FORMS

[75] Inventors: Surendra C. Mehta, Randolph; Hua-Pin Huang, Succasunna; Galen W. Radebaugh, Chester; Mahdi B. Fawzi, Flanders, all of N.J.

[73] Assignee: Warner Lambert Co., Morris Plains, N.J.

[21] Appl. No.: 966,998

[22] Filed: Oct. 27, 1992

[51] Int. Cl.$^5$ .................... A61K 31/44; A61K 31/47
[52] U.S. Cl. ..................... 514/300; 514/312
[58] Field of Search .................. 514/300, 312

[56] References Cited

U.S. PATENT DOCUMENTS

| | | | |
|---|---|---|---|
| 4,359,578 | 11/1982 | Matsumoto et al. | 514/960 |
| 4,771,054 | 9/1988 | Domagala et al. | 514/300 |
| 4,795,751 | 1/1989 | Matsumoto et al. | 514/254 |
| 4,840,954 | 6/1989 | Petersen et al. | 514/300 |
| 4,851,418 | 7/1989 | Sanchez | 514/300 |
| 4,916,141 | 4/1990 | Sanchez | 514/300 |
| 4,929,613 | 5/1990 | Culbertson et al. | 514/300 |
| 4,973,590 | 11/1990 | Preiss et al. | 514/300 |
| 5,057,520 | 10/1991 | Chu et al. | 514/300 |

OTHER PUBLICATIONS

M. Nakano; M. Yamamoto; T. Arita; *Interactions of Aluminum, Magnesium, and Calcium Ions with Nalidixic Acid*, Chem. Pharm. Bull. 26(5) 1505-1510 (1978).

C. Spurlock; *Increasing Solubility of Enoxacin and Norfloxacin by Means of Salt Formation*, Journ. of Parenteral Science & Technology, pp. 70-72. (1986).

N. B. Behrens; G. M. Diaz, *Metal Complexes of the Antibiotic Nalidixic Acid*, Inorganica Chimica Acta, 125, pp. 21-26 (1986).

W. R. Vincent; S. G. Schulman; J. M. Midgely; W. J. van Oort; R. H. A. Sorel, *Prototropic and Metal Complexation* . . . Int. Journ. of Pharmaceutics, 9(1981) pp. 191-198.

Primary Examiner—Frederick E. Waddell
Assistant Examiner—Raymond J. Henley, III
Attorney, Agent, or Firm—Krass & Young

[57] ABSTRACT

Calcium lactate antibacterial complexes in parenteral dosage forms are provided that are relatively free from tissue irritation following injection, comprising a quinolone or naphthyridine.

21 Claims, No Drawings

SOLUBLE CALCIUM LACTATE ANTIBACTERIAL COMPLEXES AS NON-IRRITATING PARENTERAL FORMS

FIELD OF THE INVENTION

The present invention relates to calcium lactate antibacterial complexes of quinolone or naphthyridine in parenteral dosage forms that are compatible (i.e., free or relatively free from tissue irritation) following injection.

BACKGROUND OF THE INVENTION

The *Journal of Parenteral Science and Technology*, Vol. 40, No. 2, 1986, pp. 70-72, describes a method of increasing solubility of anti-infective drugs enoxacin (a naphthyridine) and norfloxacin (a quinoline) by means of salt formation. The four salts found to be best were the aspartate, galacturonate, gluconate, and glutamate.

German application 3635062 covers metal salts of 1-cyclopropylquinoline carboxylic acids used as antibacterials.

European application 191,451 covers 1-cyclopropyl-5-substituted pyrrolidinyl-dihydro-oxonaphthyridines useful as antibacterials with good water solubility.

U.S. Pat. No. 4,359,578 covers the compound enoxacin (1-ethyl-6-fluoro-1,4-dihydro-4-oxo-7-(1-piperazinyl)-1,8-naphthyridine-3-carboxylic acid), methods of preparation, and the use thereof as an antibacterial agent. The patent is incorporated herein by reference.

U.S. Pat. No. 4,795,751 covers the compound 5-amino-1-cyclopropyl-6,8-difluoro-7-(3,5-methyl-1-piperazinyl)-1,4-dihydro-4-oxoquinoline-3-carboxylic acid (Compound A) methods of preparation, and the use thereof as an antibacterial agent. The patent is incorporated herein by reference.

U.S. Pat. No. 4,771,054 covers the compound 7-(3-amino-1-pyrrolidinyl)-8-chloro-1-cyclopropyl-6-fluoro-1,4-dihydro-4-oxo-3-quinoline carboxylic acid, its preparation and use as an antibacterial. The patent is incorporated herein by reference.

U.S. Pat. No. 4,851,418 covers the compound [S-(R*,R*)]-7-[3-[(2-amino-1-oxopropyl)amino]-1-pyrrolidinyl]-1-cyclopropyl-6-fluoro-1,4-dihydro-4-oxo-1,8-naphthyridine-3-carboxylic acid hydrochloride, its preparation and use as an antibacterial. The patent is incorporated herein by reference.

As a parenteral form, most quinolones and naphthyridines are used in the form of salts which provide acidic parenteral solutions. These formulations are associated with tissue irritation following injection, possibly because of the low pH of the solution.

For parenteral administration, calcium salts are relatively nontoxic compared to other divalent and trivalent salts (e.g., Zn, Mg, Al). The latter salts can cause extreme systemic toxicity. Other di- and trivalent salts besides calcium may be useful for oral formulations of quinolones/naphthyridines.

Concurrent administration of antacids has been implicated as a cause in the decrease in bioavailability of quinolones (Package Insert Cipro ® Tablets: Miles, Inc. Pharmaceutical Division; 400 Morgan Lane; West Haven, Conn. 06516).

Salts frequently contained in the antacids are calcium carbonate, magnesium hydroxide, and aluminum hydroxide. Interaction between quinolones, chiefly nalidixic acid, and metal ions have been reported. (Nakano, Masahiro; Yamamoto, Masakazu; and Arita, Takaichi; "Interactions of Aluminum, Magnesium, and Calcium Ions with Nalidixic Acid," *Chem. Pharm. Bull.*, 26 1505 (1978); Behrens, Barba Norah; and Diaz Guillermo Mendoza; "Metal Complexes of the Antibiotic Nalidixic Acid", *Inorganica Chimica Acta*, 125 21 (1986); and Vincent, W. R.; Schulman, S. G.; Midgley, J. M., van Oort, W. J.; and Sorel, R. H. A.; "Prototropic and Metal Complexation Equilibria of Nalidixic Acid in the Physiological pH Region" *International Journal of Pharmaceutics*, 9 191 (1981).

Japanese Application 63-188626 discloses aluminum, zinc, and magnesium compounds for solubilizing amphoteric pyridine carboxylic acids or their salts. These metals have been reported to be toxic, especially when administered parenterally. The reference mentions the addition of sodium, potassium, and calcium chloride to pyridine carboxylic acids. It does not disclose the preparation of sodium, calcium and potassium salts of pyridine carboxylic acid.

SUMMARY AND DETAILED DESCRIPTION

In one aspect, the invention concerns a soluble calcium lactate antibacterial complex in parenteral dosage form, comprising lactic acid, calcium hydroxide, and an antibacterial compound. The antibacterial compound is selected from 1) a quinolone of formula

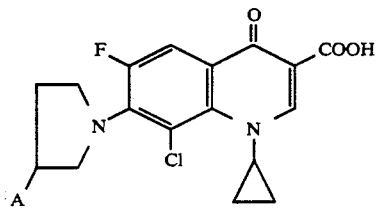

where A is aminomethyl, ethylaminomethyl or amino; 2) a naphthyridine of formula

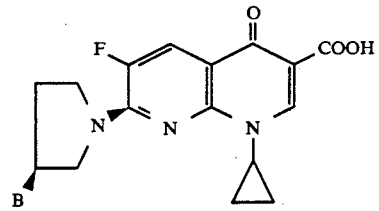

or an optical isomer thereof, where B is 2-amino-1-oxopropylamino, aminoacetylamino, (2-amino-1-oxo-3-phenylpropyl)amino, (2,5-diamino-1,5-dioxopentyl)amino, (2-amino-4-carboxy-1-oxobutyl)amino, (2,6-diamino-1-oxohexyl) amino, or (aminopheylacetyl)amino; or 3) a naphthyridine of formula

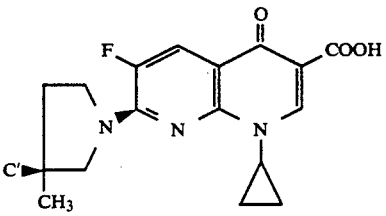

or an optical isomer thereof, where C' is [(2-amino-1-oxo-3-phenylpropyl)amino]methyl, [(2-amino-1-oxopropyl)amino]methyl, [(aminoacetyl)amino]methyl, [(aminophenylacetyl)amino]methyl, [(2-amino-4-carboxy-1-oxobutyl)amino]methyl, [(2,6-diamino-1-oxohexyl)amino]methyl, or [(2,5-diamino-1,5-dioxopentyl)amino]methyl.

In one preferred embodiment, the antibacterial compound is 7-(3-amino-1-pyrrolidinyl)-8-chloro-1-cyclopropyl-6-fluoro-1,4-dihydro-4-oxo-3quinolinecarboxylic acid. In another preferred embodiment, the antibacterial compound is [S-(R*,R*)]-7-[3-[(2-amino-1-oxopropyl)amino]-1-pyrrolidinyl]-1-cyclopropyl-6-fluoro-1,4-dihydro-4-oxo-1,8-naphthyridine-3-carboxylic acid.

The complex in a preferred embodiment is produced by dissolving an antibacterially effective quantity of the antibacterial compound in an aqueous lactic acid solution, preferably L-(+)-lactic acid solution, neutralizing the resulting solution with calcium hydroxide in a quantity that is selected so that any precipitation of the antibacterial compound from the solution is avoided and yet on intravenous injection, venous irritation by the neutralized solution is either absent or is minimized. The quantity of lactic acid preferably is from 1 to 3 moles and more preferably about 1.6 moles per mole of the carboxylic acid. The amount of calcium hydroxide is that amount sufficient to raise the pH of the injectable solution between about 4.0 to about 5.5. The resulting neutralized solution is then processed by sterile filtration to provide a sterile solution. The sterile solution is preferably lyophilized (freeze-dried) to provide a dry product that is stable for extended periods.

For use as an intravenous infusion, a liquid product is obtained by reconstitution of the dry product in an intravenous infusion fluid such as saline (0.9% NaCl), 5% dextrose solution, Ringer's solution, lactated Ringer's solution, and the like. Upon reconstitution, the product preferably has a pH in the range from about 4 to about 5.5, more preferably about 4.8.

A formula for preparation of a dry product suitable for reconstitution in an infusion fluid is the following:

| Ingredients | Amount |
| --- | --- |
| 1. Antibacterial | 30.0 g* |
| 2. L-(+)-lactic acid | 12.0 g |
| 3. Calcium hydroxide, USP | 1.9 g |
| 4. Water for injection, USP | 1000 ml |
| 5. Nitrogen gas high purity | q.s. |

*Amount used should be corrected to 100% based on purity and moisture.

Procedure: Dissolve 2 in approximately 900 ml of 4 in a suitable container and mix well. Add 1 with mixing until all the drug particles are dissolved. Add 3 with mixing. Check pH (ca. 4.6–4.9); adjust pH with calcium hydroxide or lactic acid if necessary. Sterilize the solution by filtering through a previously sterilized 0.22 μm membrane or equivalent (Millipore 293 mm assembly or Millipack 100) using 5 for positive pressure. Discard 100 ml of solution to flush the system. Aseptically fill 10.05–10.1 ml of the solution into previously sterilized and depyrogenated vials. Stopper loosely with slotted closures and lyophilize. Stopper and cap the lyophilized vials.

The above product was prepared in 20 c.c. Type I, amber tubing vials with 20 mm neck. When reconstituted with 10 ml of sterile water for injection, the resultant solution contains 30 mg/ml of free base equivalent. The solution typically is greenish yellow with a pH of 4.8. The product prepared as above by aseptic filtration followed by lyophilization provides a suitable dissolution rate for reconstitution. The product can be redissolved in 0.9% NaCl, 5% Dextrose solution, Ringer's solution and lactated Ringer's solution for use in the hospital.

Having described the invention, the embodiments thereof in which an exclusive property or privilege is claimed are defined as follows:

1. A storage stable soluble calcium lactate antibacterial complex in parenteral dosage form, comprising in solution a) a lactic acid salt of a carboxylic acid antibacterial compound corresponding to 1 to 3 moles of lactic acid per mole of the antibacterial compound, the antibacterial compound being selected from 1) a quinolone of formula

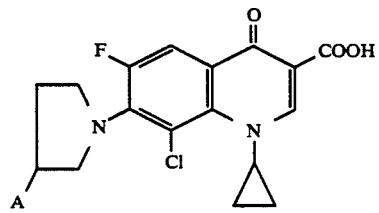

wherein A is aminomethyl, ethylaminomethyl or amino;

2) a naphthyridine of formula

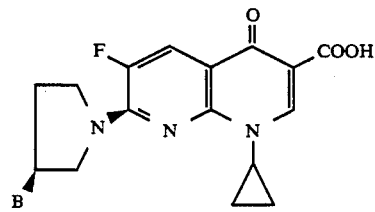

or an optical isomer thereof, wherein B is 2-amino-1-oxopropylamino, amnioacetylamino, (2-amino-1-oxo-3-phenylpropyl)amino, (2,5-diamino-1,5-dioxopentyl)amine, (2-amino-4-carboxy-1-oxobutyl)amino, (2,6-diamino-1-oxohexyl)amino, or (aminophenylacetyl)amino, or 3) a naphthyridine of formula

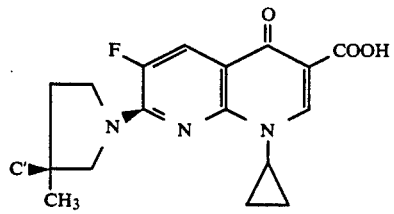

or an optical isomer thereof, wherein C' is [(2-amino-1-oxo-3-phenylpropyl)amino]methyl, [(2-amino-1-oxopropyl)amino]methyl, [(aminoacetyl)amino]methyl, [(aminophenylacetyl)amino]methyl, [(2-amino-4-carboxy-1-oxobutyl)amino]methyl, [(2,6-diamino-1-oxohexyl)amino]methyl, or [(2,5-diamino-1,5-dioxopentyl)amino]methyl;

and b) calcium hydroxide in a quantity that is selected so that the pH of the solution is between about 4.0 to about 5.5, precipitation of the antibacterial compound from the solution is avoided and yet on injection irritation by the solution is absent or minimized.

2. A sterile filtered solution according to claim 1.

3. A lyophilized dry product form of the sterile solution according to claim 2.

4. A liquid product form obtained by reconstruction of the dry product according to claim 3 reconstituted in an infusion fluid.

5. A liquid product according to claim 4 where the infusion fluid is selected from saline, 5% dextrose solution, Ringer's solution, and lactated Ringer's solution.

6. A liquid product according to claim 4 having a pH in the range from about 4 to about 5.5.

7. A calcium lactate product according to claim 1 where said lactic acid is L-(+)-lactic acid.

8. A storage stable calcium lactate antibacterial complex in parenteral dosage form, comprising in solution a) a lactic acid salt of 7-(3-amino-1-pyrrolidinyl)-8-chloro-1-cyclopropyl-6-fluoro-1,4-dihydro-4-oxo-3-quinolinecarboxylic acid corresponding to 1 to 3 moles of lactic acid per mole of the carboxylic acid, and b) calcium hydroxide in a quantity selected so that the pH of the solution is between about 4.0 to about 5.5, precipitation of the carboxylic acid from the solution is avoided, and yet on injection irritation by the solution is absent or minimized.

9. A sterile filtered solution according to claim 8.

10. A lyophilized dry product form of the sterile solution according to claim 9.

11. A liquid product form of the dry product according to claim 10 in an infusion fluid.

12. A liquid product according to claim 11 where the infusion fluid is selected from saline, 5% dextrose solution, Ringer's solution, and lactated Ringer's solution.

13. A liquid product according to claim 11 having a pH in the range from about 4 to about 5.5.

14. A calcium lactate product according to claim 8 where said lactic acid is L-(+)-lactic acid.

15. A storage stable calcium lactate antibacterial complex in parenteral dosage form, comprising in solution a) a lactic acid salt of [S-(R*,R*)]-7-[3-[(2-amino-1-oxopropyl)amino]-1-pyrrolidinyl]-1-cyclopropyl-6-fluoro-1,4-dihydro-4-oxo-1,8-naphthyridine-3-carboxylic acid corresponding to 1 to 3 moles of lactic acid per mole of carboxylic acid and b) calcium hydroxide in a quantity selected so that the pH of the solution is between about 4.0 to 5.5, precipitation of the carboxylic acid from the solution is avoided, and yet on injection irritation by the solution is absent or minimized.

16. A sterile filtered solution according to claim 15.

17. A lyophilized dry product of the sterile solution according to claim 16.

18. A liquid product form of the dry product according to claim 17 in an infusion fluid.

19. A liquid product according to claim 18 where the infusion fluid is selected from saline, 5% dextrose solution, Ringer's solution, and lactated Ringer's solution.

20. A liquid product according to claim 18 having a pH in the range from about 4 to about 5.5.

21. A calcium lactate product according to claim 15 where said lactic acid is L-(+)-lactic acid.

* * * * *

UNITED STATES PATENT AND TRADEMARK OFFICE
CERTIFICATE OF CORRECTION

PATENT NO. : 5,290,794

DATED : March 1, 1994

INVENTOR(S) : Mehta et al.

It is certified that error appears in the above-identified patent and that said Letters Patent is hereby corrected as shown below:

Column 3, line 8, delete "3quinolinecarboxylic" and insert --3-quinolinecarboxylic--;

Column 4, line 41, delete "amnioacetylamino" and insert --aminoacetylamino--;

Column 4, line 43, delete "opentyl)amine" and insert --opentyl)amino--.

Signed and Sealed this

Twenty-sixth Day of July, 1994

Attest:

BRUCE LEHMAN

Attesting Officer     Commissioner of Patents and Trademarks